US007357940B2

(12) United States Patent
Richard et al.

(10) Patent No.: US 7,357,940 B2
(45) Date of Patent: Apr. 15, 2008

(54) IMPLANTABLE OR INSERTABLE MEDICAL DEVICES CONTAINING GRAFT COPOLYMER FOR CONTROLLED DELIVERY OF THERAPEUTIC AGENTS

(75) Inventors: Robert E. Richard, Wrentham, MA (US); Frederick H. Strickler, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 623 days.

(21) Appl. No.: 10/632,413

(22) Filed: Jul. 31, 2003

(65) Prior Publication Data

US 2005/0025803 A1 Feb. 3, 2005

(51) Int. Cl.
*A61F 13/00* (2006.01)
(52) U.S. Cl. ............. 424/422; 604/890.1; 604/891.1
(58) Field of Classification Search ............. 424/422; 604/890.1, 891.1
See application file for complete search history.

(56) References Cited

U.S. PATENT DOCUMENTS

| | | | |
|---|---|---|---|
| 4,196,731 A | 4/1980 | Laurin et al. | 128/214 R |
| 4,861,830 A | 8/1989 | Ward, Jr. | 525/92 |
| 4,946,899 A | 8/1990 | Kennedy et al. | 525/244 |
| 4,951,656 A | 8/1990 | Gorka et al. | 128/90 |
| 5,258,020 A | 11/1993 | Froix | 623/1 |
| 5,266,645 A * | 11/1993 | Siol et al. | 525/309 |
| 5,304,121 A | 4/1994 | Sahatjian | 604/53 |
| 5,616,608 A | 4/1997 | Kinsella et al. | 514/449 |
| 5,716,981 A | 2/1998 | Hunter et al. | 514/449 |
| 5,733,925 A | 3/1998 | Kunz et al. | 514/449 |
| 5,741,331 A | 4/1998 | Pinchuk | 623/11 |
| 5,814,329 A * | 9/1998 | Shah | 424/433 |
| 5,856,367 A | 1/1999 | Barrows et al. | 521/64 |
| 5,879,697 A | 3/1999 | Ding et al. | 424/422 |
| 5,916,968 A * | 6/1999 | Hariharan et al. | 525/54.2 |
| 5,954,706 A | 9/1999 | Sahatjian | 604/509 |
| 6,099,562 A | 8/2000 | Ding et al. | 623/1.46 |
| 6,280,411 B1 | 8/2001 | Lennox | 604/103.05 |
| 6,335,029 B1 | 1/2002 | Kamath et al. | 424/423 |
| 2002/0045706 A1 | 4/2002 | Houston et al. | 525/100 |
| 2002/0107330 A1* | 8/2002 | Pinchuk et al. | 525/242 |
| 2003/0039689 A1* | 2/2003 | Chen et al. | 424/468 |

FOREIGN PATENT DOCUMENTS

| | | |
|---|---|---|
| DE | 3245633 A1 | 6/1984 |
| GB | 2271717 A * | 4/1994 |
| WO | WO 98/37111 | 8/1998 |
| WO | WO 2004/000381 A1 | 12/2003 |
| WO | WO 2004/000384 A1 | 12/2003 |

OTHER PUBLICATIONS

"Ethylene vinyl acetate". PolySciences, Inc. Online. Accessed Dec. 6, 2006. <http://www.polysciences.com/shop/product.asp?pf_id=24763&dept_id=300165>.*
"shunt". Stedman's Medical Dictionary 27th Ed., accessed online on May 23, 2007. <http://www.thomsonhc.com>.*
Joseph C. Salamone, ed., *Concise Polymeric Materials Encyclopedia* (Boca Raton, FL: CRC Press, 1999), pp. 812-814.
Richard G. Jones et al., "A Convenient Route to Poly (methylphenylsilane)-*Graft*-Polystyrene Copolymers," Macromol. Chem. Phys., 198 (1997), pp. 3571-3579.
L.H. Sperling, *Polymeric Multicomponent Materials* (New York: John Wiley, 1997), pp. 275-325.
Linda S. Flosenzier et al., "The Effects of Blending Small Amounts of Homopolystyrene on the Mechanical Properties of a Low Styrene Content Styrene-Butadiene-Styrene Block Copolymer," *Polymer Engineering and Science*, vol. 30, No. 1 (mid-Jan. 1990), pp. 49-58.
James F. Beecher et al., "Morphology and Mechanical Behavior of Block Polymers," *Journal of Polymer Science*, Part C, No. 26 (1969), pp. 117-134.
*Diblock and Triblock Copolymers*, pp. 141-151.
Kohtaro Kimishima et al., "Control of Self-Assembled Structures in Binary Mixtures of A-B Diblock Copolymer and A-C Diblock Copolymer by Changing the Interaction between B and C Block Chains," Macromolecules, 32 (1999), pp. 2585-2596.
Richard J. Spontak et al., "Phase Behavior of Ordered Diblock Copolymer Blends: Effect of Compositional Heterogeneity," *Macromolecules*, 29 (1996), pp. 4494-4507.
Hong G. Jeon et al., "Microphase and Macrophase Transitions in Binary Blends of Diblock Copolymers," *Macromolecules*, 32 (1999), pp. 1803-1808.
Immiscible Polymer Blends, http://www.psrc.usm/macrog/iblend.htm.
L.H. Sperling, *Polymeric Multicomponent Materials: An Introduction* (New York: John Wiley), pp. 284-285.
Reference: Polymer Properties. http://www.sigmaaldrich.com/img/assets/3900/Thermal_Transitions_of_Homopolymers.pdf.
The Glass Transition. http://www.psrc.usm.edu/macrog/tg.htm.
Database WPI, Section CH, Week 198449, Derwent Publications Ltd., London, Class A18, AN 1984-303740 and JP 59 189153 A, Terumo Corp., Oct. 26, 1984, abstract.

* cited by examiner

*Primary Examiner*—Carlos A. Azpuru
*Assistant Examiner*—Casey Hagopian
(74) *Attorney, Agent, or Firm*—Mayer & Williams PC; David B. Bonham, Esq.; Keum J. Park, Esq.

(57) ABSTRACT

Implantable or insertable medical devices are described. The medical devices comprise (a) a therapeutic agent and (b) a polymeric release region that controls the release of the therapeutic agent upon administration to a patient. The polymer release region comprises a graft copolymer, which further comprises a main chain and a plurality of side chains. One of (a) the main chain and (b) the side chains corresponds to a rubbery phase within the release region at ambient temperatures, while the other corresponds to a hard phase within the release layer at ambient temperatures. Typically, the graft copolymer will comprise one glass transition temperature below ambient temperature and another second glass transition temperature above ambient temperature. Also described are methods for forming the above graft copolymers, methods for administering a therapeutic agent to a patient using the above implantable or insertable medical devices, as well as methods for making the above devices.

21 Claims, No Drawings

US 7,357,940 B2

IMPLANTABLE OR INSERTABLE MEDICAL DEVICES CONTAINING GRAFT COPOLYMER FOR CONTROLLED DELIVERY OF THERAPEUTIC AGENTS

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. Accordingly, there is a continuing need for polymeric materials that can serve as release regions, such as barrier layers and/or carrier layers, which are able to provide a range of therapeutic agent release rates.

SUMMARY OF THE INVENTION

The present invention is directed to novel implantable or insertable medical devices, which provide controlled release of a therapeutic agent.

According to a first aspect of the present invention, an implantable or insertable medical device is provided, which comprises (a) a therapeutic agent and (b) a polymeric release region that controls the release of the therapeutic agent upon administration to a patient. The polymer release region comprises a graft copolymer, which further comprises a main chain and a plurality of side chains. One of (a) the main chain and (b) the side chains corresponds to a rubbery phase within the release region at ambient temperatures, while the other corresponds to a hard phase within the release layer at ambient temperatures. Typically, the graft copolymer will comprise a first glass transition temperature below ambient temperature and a second glass transition temperature above ambient temperature.

In some embodiments, the main chain corresponds to the rubbery phase within the release region, while the side chains correspond to the hard phase. Typically, the main chain will comprise a low $T_g$ monomer (e.g., a monomer having a glass transition temperature lower that ambient temperature, more typically below 25° C., 0° C., −25° C., or even −50° C. when in homopolymer form) and the side chains will comprise a high $T_g$ monomer (e.g., a monomer having a glass transition temperature higher than ambient temperature, more typically above 50° C., 60° C., 70° C., 80° C., 90° C. or even 100° C., when in homopolymer form). Examples of main chains corresponding to rubbery phases are those comprising poly(methyl acrylate), poly(ethyl acrylate) or poly(butyl acrylate), whereas examples of side chain corresponding to hard phases are those comprising poly(styrene) or poly(methyl methacrylate).

In other embodiments, the main chain corresponds to the hard phase within the release region, while the side chains correspond to the rubbery phase. Typically, the main chain will comprise a high $T_g$ monomer and the side chains will comprise a low $T_g$ monomer. Examples of main chains corresponding to hard phases are those comprising poly(styrene) or poly(methyl methacrylate), whereas examples of side chains corresponding to rubbery phases are those comprising poly(methyl acrylate), poly(ethyl acrylate) or poly(butyl acrylate).

In many embodiments, the graft copolymer is one having an elongation at break of at least 25% at ambient temperature.

The polymeric release region of the implantable or insertable medical device can be, for example, (a) a carrier region that comprises the therapeutic agent or (b) a barrier region that is disposed over a therapeutic-agent-containing region that comprises the therapeutic agent. In certain embodiments, the polymeric release region is in the form of a coating layer.

Examples of implantable or insertable medical device include catheters, guide wires, balloons, filters, stents, stent grafts, vascular grafts, vascular patches, and shunts. The implantable or insertable medical device may be adapted for implantation or insertion into, for example, the coronary vasculature, peripheral vascular system, esophagus, trachea, colon, biliary tract, urinary tract, prostate or brain.

The therapeutic agent can be selected from any number of categories, including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

The above graft copolymers can be formed by a number of techniques. As a first example, the graft copolymer can be formed by a method that comprises (i) reacting (e.g., by free radical polymerization or metallocene polymerization reaction) a side chain monomer comprising a previously formed chain and a reactive group (e.g., an unsaturated group) with (ii) a main chain monomer comprising a previously formed chain and a plurality of reactive side groups (e.g., unsaturated groups).

As another example, the graft copolymer can be formed by a method that comprises reacting (i) a side chain monomer comprising a previously formed chain and a reactive group with (ii) an additional monomer comprising a reactive group, thereby forming the main chain in situ.

As another example, the graft copolymer can be formed by a method that comprises reacting (i) a main chain monomer comprising a previously formed chain and a plurality of reactive side groups with (ii) an additional monomer comprising a reactive group, thereby forming the side chain in situ.

The above medical devices can also be formed by a number of techniques. According to an embodiment of the invention, a method of forming the above implantable or insertable medical devices is provided, which comprises: (a) providing a solution comprising (i) a solvent (which comprises one or more solvent species) and (ii) the graft copolymer; and (b) forming the release region from the solution by removing the solvent from the solution. For example, the solution can be applied to a medical device surface (e.g., by spraying). In some embodiments (for example, where a carrier region is formed), the solution can further comprise the therapeutic agent in dissolved or dispersed form. In other embodiments (for example, where a barrier region is formed), the solution is applied over a therapeutic-agent-containing region.

According to another aspect of the present invention, a method is provided for releasing a therapeutic agent within a patient. The method comprises (a) providing one of the above implantable or insertable medical devices and (b) implanting or inserting the therapeutic-agent-releasing medical device into the patient.

In certain embodiments, the medical device is inserted into the vasculature, where the therapeutic agent is released for example, in the treatment of restenosis. Upon implantation or insertion of the device into the patient, the release of the therapeutic agent from the device can correspond, for example, to a sustained release profile.

One advantage of the present invention is that implantable or insertable medical devices can be provided, which provide for controlled release of a therapeutic agent.

Another advantage of the present invention is that a variety of materials can be provided, which can be used in release regions of implantable or insertable medical devices.

Another advantage of the present invention is that implantable or insertable medical device release regions can be provided, which comprise a polymer that can be formed using a variety of polymerization techniques.

Yet another advantage of the present invention is that implantable or insertable medical device release regions can be provided, which comprise a polymer whose chemical composition can be readily modified, for example, to improve the drug releasing properties or radiation resistance of the same.

These and other embodiments and advantages of the present invention will become immediately apparent to those of ordinary skill in the art upon review of the Detailed Description and claims to follow.

DETAILED DESCRIPTION OF THE INVENTION

The present invention relates to implantable or insertable medical devices comprising (a) a therapeutic agent and (b) a polymeric release region that controls the release of said therapeutic agent upon administration to a patient.

The polymeric release region can be provided in a number of configurations. For example, the polymeric release region can constitute the entirety of the medical device, or it can constitute only a portion of the medical device. The portion of the medical device can be, for example, one or more medical device layers (e.g., one or more coating layers), one or medical device components or portions thereof, and so forth.

By "release region" is meant a region that regulates the rate of release of a therapeutic agent. Release regions are commonly either carrier regions or barrier regions. A "carrier region" is region which contains at least one therapeutic agent and from which the therapeutic agent is released. A "barrier region" is a region that is disposed between a source of therapeutic agent and a site of intended release, which controls the rate at which the therapeutic agent is released.

For instance, in some embodiments of the present invention, an outer carrier layer is disposed over at least a portion of an implantable or insertable medical device substrate. Upon implantation or insertion of the device, the therapeutic agent is released from the carrier layer in a controlled fashion. In other embodiments, a therapeutic-agent-containing layer and a barrier layer are provided over at least a portion of an implantable or insertable medical device substrate. Because the barrier layer is disposed over the therapeutic-agent-containing layer, the barrier layer acts to control release of the therapeutic agent from the medical device upon implantation or insertion of the same.

Release region thickness can be varied to control the release of therapeutic agent. Moreover, multiple release regions can be employed to achieve this end. In addition, where a carrier region is employed, a therapeutic-agent concentration gradient can be established within the carrier region to control release of therapeutic agent.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent that delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

The present invention utilizes polymeric release regions comprising one or more graft copolymers. As used herein, a "polymer" is a molecule having one or more chains within which multiple copies of one or more constitutional units are found. A specific example of a polymer is polystyrene

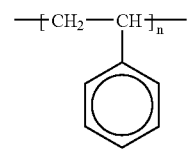

in which n styrene constitutional units are found.

A copolymer is a polymer that contains at least two differing constitutional units. Typically, at least 10, 50, 100, 500, 1000 or even more of each constitutional unit is found in the copolymers of the present invention.

Graft copolymers are copolymers having a main chain and one or more side chains that are constitutionally different from the main chain. Typically, the graft copolymers of the present invention contain main and side chains that are constitutionally different from one another because they are derived from different characteristic species of monomer (e.g., because a monomer found in the main chain is not found in the side chains and/or vice versa).

The main and side chains of the graft copolymers of the present invention can assume a number of configurations including: (a) chains having repeating constitutional units of a single type (e.g., a chain containing a single monomer block), (b) chains having repeating constitutional units of two or more types (e.g., a chain containing two distinct monomer blocks), (c) chains with randomly distributed constitutional units of two or more types (e.g., a random copolymer chain of two monomers), (d) chains in which two or more constitutional units repeat within a series (e.g., an alternating copolymer chain of two monomers), and so forth.

The graft copolymers that are used in connection with the present invention typically fall into one of two classes: (1) graft copolymers having (a) a main chain that results in the formation of a rubbery phase within the release layer at ambient temperatures and (b) at least one side chain that results in the formation of a hard phase within the release layer at ambient temperatures and (2) graft copolymers having (a) a main chain that results in the formation of a hard phase within the release layer at ambient temperatures and (b) at least one side chain that results in the formation of a rubbery phase within the release layer at ambient temperatures. Such polymers typically have good strength, while also being elastomeric, and hence capable of expansion. This is a particularly desirable feature for expandable medical devices such as balloons and expandable stents. Ambient temperature is typically 25° C.-45° C., more typically body temperature (e.g., 35° C.-40° C.).

In certain embodiments of the present invention, the chains forming the hard and rubbery phases are selected on the basis of glass transition temperature. For example, chains that result in the formation of a rubbery phase within the release region at ambient temperature are typically based on "low $T_g$ monomers," which are monomers that can display a glass transition temperature ($T_g$) as measured by any of a number of techniques including differential scanning calorimetry, dynamic mechanical analysis, or thermomechanical analysis, which is below ambient temperature, more typically below 25° C., 0° C., −25° C., or even −50° C., when the monomer is in homopolymer form. Similarly, chains that result in the formation of a hard phase within the release region at ambient temperature are typically based on "high $T_g$ monomers," which are monomers that can display either (a) a $T_g$ or (b) a melting point ($T_m$) as measured by any of a number of techniques including differential scanning calorimetry, which is above ambient temperature, more typically above 50° C., 60° C., 70° C., 80° C., 90° C. or even 100° C., when the monomer is in homopolymer form. Commonly, the resulting graft copolymer itself will itself have two glass transition temperatures, one above ambient temperature and another below ambient temperature.

Examples of monomers that can exhibit a supra-ambient $T_g$ or a supra-ambient $T_m$ when in homopolymer form include, for example, vinyl aromatic monomers, other vinyl monomers, other aromatic monomers, methacrylic monomers, acrylic monomers, and alkenes.

Vinyl aromatic monomers are those having aromatic and vinyl moieties and include unsubstituted monomers, vinyl-substituted monomers and ring-substituted monomers. Suitable vinyl aromatic monomers include the following (listed along with a published homopolymer $T_g$ and, in some instances, a published homopolymer $T_m$): (a) unsubstituted vinyl aromatics, such as atactic styrene ($T_g$ 100° C.), isotactic styrene ($T_g$ 100° C.) ($T_m$ 240° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylsytrene ($T_g$ 97° C.), 4-methylsytrene ($T_g$ 97° C.), 2,4-dimethylsytrene ($T_g$ 112° C.), 2,5-dimethylsytrene ($T_g$ 143° C.), 3,5-dimethylsytrene ($T_g$ 104° C.), 2,4,6-trimethylsytrene ($T_g$ 162° C.), and 4-tert-butylstyrene ($T_g$ 127° C.), (ii) ring-alkoxylated vinyl aromatics, such as 4-methoxysytrene ($T_g$ 113° C.) and 4-ethoxysytrene ($T_g$ 86° C.), (iii) ring-halogenated vinyl aromatics such as 2-chlorosytrene ($T_g$ 119° C.), 3-chlorosytrene ($T_g$ 90° C.), 4-chlorosytrene ($T_g$ 100° C.), 2,6-dichlorosytrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Other suitable vinyl monomers include the following: (a) vinyl alcohol ($T_g$ 85° C.) ($T_m$ 220° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl private ($T_g$ 86° C.), vinyl trifluoroacetate ($T_g$ 46° C.), vinyl butyral ($T_g$ 49° C.) ($T_m$ 322° C.), (c) vinyl amines such as 2-vinyl pyridine ($T_g$ 104° C.), 4-vinyl pyridine ($T_g$ 142° C.), and vinyl carbazole ($T_g$ 227° C.) ($T_m$ 320° C.), (d) vinyl halides such as vinyl chloride ($T_g$ 81° C.) ($T_m$ 227° C.) and vinyl fluoride ($T_g$ 40° C.) ($T_m$ 171° C.); (e) alkyl vinyl ethers such as methyl vinyl ether ($T_g$ −3°° C.) ($T_m$ 144° C.), propyl vinyl ether ($T_g$ −49° C.) ($T_m$ 76° C.), butyl vinyl ether ($T_g$ −55° C.) ($T_m$ 64° C.), isobutyl vinyl ether ($T_g$ −19° C.) ($T_m$ 165° C.), tert-butyl vinyl ether ($T_g$ 88° C.) ($T_m$ 250° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Suitable aromatic monomers, other than the above vinyl aromatics, include acenaphthalene ($T_g$ 214° C.) and indene ($T_g$ 85° C.).

Suitable methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.) ($T_m$ 200° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Suitable acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ −11° C.) ($T_m$ 162° C.), tert-butyl acrylate ($T_g$ 43-107° C.) ($T_m$ 193° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.) ($T_m$ 319° C.).

Suitable alkene based monomers include the following: ethylene (HDPE) ($T_g$ −125° C.) ($T_m$ 130° C.), isotactic propylene ($T_g$ −8° C.) ($T_m$ 176° C.), 4-methyl pentene ($T_g$ 29° C.) ($T_m$ 250° C.), 1-octadecene ($T_g$ 55° C.), and tetrafluoroethylene ($T_g$ 117° C.) ($T_m$ 327° C.).

Examples of monomers that can exhibit a sub-ambient $T_g$ when in homopolymer form include, for example, acrylic monomers, methacrylic monomers, vinyl ether monomers, cyclic ether monomers, ester monomers, unsaturated hydrocarbon monomers, halogenated unsaturated hydrocarbon monomers, siloxane monomers, and other monomers.

Suitable acrylic monomers include (a) alkyl acrylates such as methyl acrylate ($T_g$ 110° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.).

Suitable methacrylic monomers include (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.).

Suitable vinyl ether monomers include (a) alkyl vinyl ethers such as methyl vinyl ether ($T_g$ −31° C.), ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.).

Suitable cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.).

Suitable ester monomers (other than acrylates and methacrylates) include ethylene malonate ($T_g$ −29° C.), vinyl acetate ($T_g$ 30° C.), and vinyl propionate ($T_g$ 10° C.).

Suitable unsaturated hydrocarbon monomers include ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.).

Suitable halogenated unsaturated hydrocarbon monomers include vinylidene chloride ($T_g$ −18° C.), vinylidene fluoride ($T_g$ 40° C.), cis-chlorobutadiene ($T_g$ −20° C.), and trans-chlorobutadiene ($T_g$ 40° C.).

Suitable siloxane monomers include dimethylsiloxane ($T_g$ −127° C.), diethylsiloxane, methylethylsiloxane, methylphenylsiloxane ($T_g$ −86° C.), and diphenylsiloxane.

Suitable additional monomers include ε-caprolactone ($T_g$ −60° C.).

The graft copolymers of the present invention beneficially have an elongation at break of at least 25% at ambient temperature in some embodiments. "Elongation" is an increase in length of a test specimen under tension, stated herein as a percentage of the original length. "Elongation at break" is the amount of elongation that is observed at the point where the specimen breaks or otherwise fails under tension.

The graft copolymers of the present invention can be synthesized using a wide variety of synthesis schemes. For instance, the use of reactive groups, for example, unsaturated groups, opens up a number of reaction chemistries including cationic polymerization, anionic polymerization, Ziegler-Natta polymerization, metallocene polymerization, free-radical polymerization, nitroxide-mediated polymerization (NMP), atom transfer radical polymerization (ATRP), and reversible addition-fragmentation chain transfer (RAFT) polymerization chemistries.

Graft copolymers can be constructed, for example, by (a) reacting a first chain having a reactive group (e.g., terminal unsaturation) with a second chain having a number of reactive side groups (e.g., unsaturated side groups), (b) reacting a first chain having a reactive group (e.g., terminal unsaturation) with a monomer (e.g., an unsaturated monomer), thus polymerizing the main chain in situ, and (c) reacting a first chain having a number of reactive side groups (e.g., unsaturated side groups) with a monomer (e.g., an unsaturated monomer), thus polymerizing the side chains in situ.

In accordance with the second strategy above (i.e., reacting a first chain having a reactive group with a monomer, thus polymerizing the main chain in situ), for example, a side chain monomer can be provided, which comprises (i) the side chains that are found in the resulting graft copolymer as well as (ii) a reactive group (e.g., an unsaturated group such as a >C═C< group) that is capable of taking part in a chain growth polymerization process. Because they contain the entire length of the side chains that are found in the resulting copolymer, such side chain monomers are also referred to herein as macro-monomers or "macromers". The side chain monomer are beneficially of sufficiently high molecular weight (i.e., the side chains are sufficiently long) to effect phase separation within the resulting graft copolymer. Preferably, the unsaturated groups are positioned at one end of the side chain monomer. Examples of unsaturated groups that can be included within the side chain monomer include vinyl groups (e.g., $H_2C$═CH— groups) and substituted vinyl groups (e.g., $H_2C$═CR— groups) where R is an organic radical. In this particular reaction scheme, the monomers that are used to form the main chain can also comprise an unsaturated group that is capable of taking part in a chain growth polymerization process. The main chain is formed upon chain growth polymerization via the unsaturation found in the main chain monomers and the unsaturated groups of the side chain monomers.

Three specific examples based on free radical and metallocene polymerization reactions are presented below. Such reactions are desirable, as they are relatively non-stringent and/or allow a wide variety of monomers to be used.

As a first specific example, chain growth polymerization of (a) a low $T_g$ acrylic monomers such as methyl acrylate and (b) side chain monomers (macromers), consisting of polystyrene having a terminal methacrylate group, is conducted in the presence of a free radical initiator as follows:

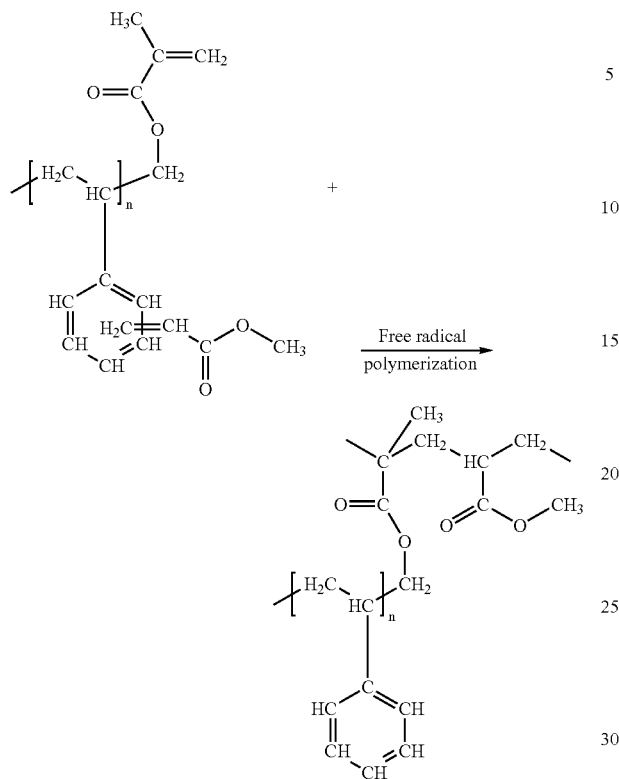

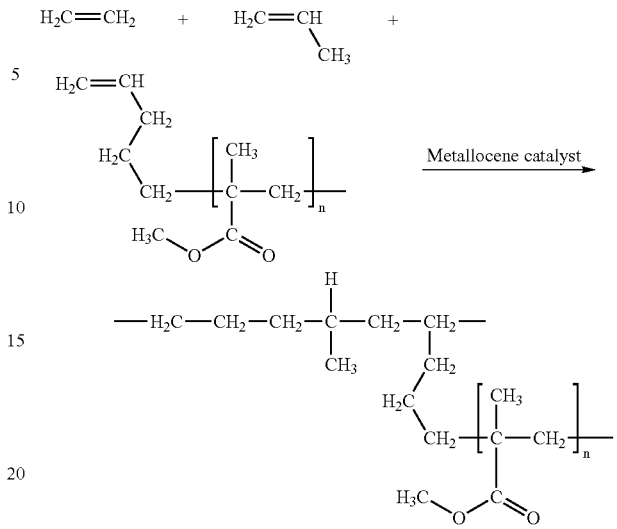

Although only two monomers are illustrated as forming the main chain, the actual polymer will obviously contain numerous monomers, with the result being a single main chain with multiple side chains.

Block copolymers containing blocks of polystyrene and polyisobutylene are known. For example, linear polystyrene-polyisobutylene-polystyrene triblock copolymers (SIBS copolymers), described in U.S. patent application 20020107330 entitled "Drug delivery compositions and medical devices containing block copolymer," are thermoplastic elastomers having an elastomeric center block and phase separated, hard polystyrene end blocks. Such copolymers are used in drug-releasing coronary stent coatings and exhibit outstanding biocompatibility and biostability. Moreover, being elastomeric, such copolymers expand as the stent is expanded.

However, SIBS copolymers are presently made using a living cationic polymerization process that is conducted at low temperatures and under stringent conditions. In addition, there are only a limited number of monomers that can be polymerized using this polymerization process, restricting the ability to vary the chemical composition of polymers made by this process. The use of side chain monomers (also referred to as macromers) in connection with the present invention, on the other hand, allows for the use of less demanding polymerization techniques to be employed, such as the above free radical polymerization process, which can be carried out at higher temperatures, under less stringent conditions and with a wider variety of monomers.

As a second specific example, chain growth polymerization of (a) ethylene monomers, (b) propylene monomers, and (c) side chain monomers (macromers) consisting of a pentenyl terminated poly(methyl methacrylate) is conducted in the presence of a metallocene catalyst as follows:

As above, although only three monomers are illustrated as forming the main chain, the actual polymer will obviously contain many monomers of each type, resulting a single main chain with multiple side chains.

As a third specific example, chain growth polymerization of (a) ethyl acrylate monomers and (b) side chain monomers of methacrylate terminated polystyrene (e.g., polystyrene having a terminal methacrylate group available from Sigma-Aldrich) is conducted in the presence of a free radical initiator as follows:

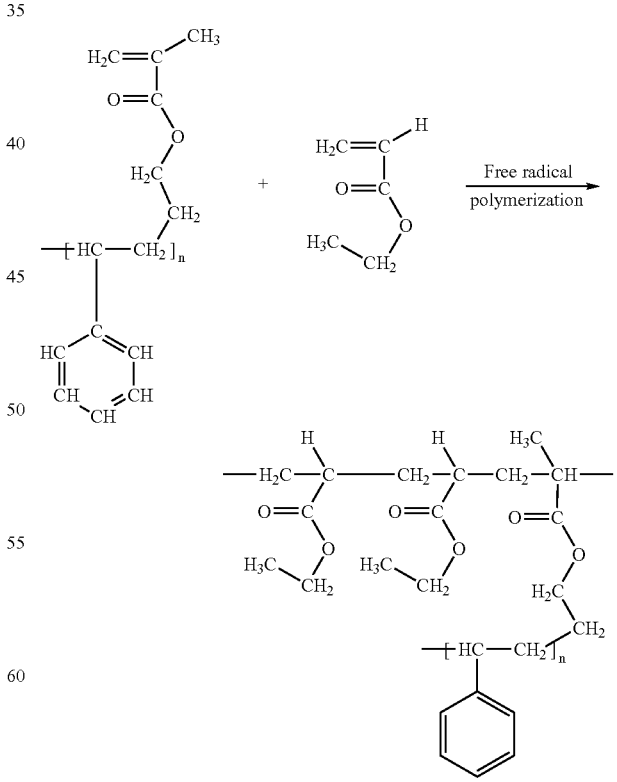

Again, although only three monomers (two ethyl acrylate monomers and one side chain monomer) are illustrated as forming the polymer chain above, the actual polymer chain will obviously contain numerous monomers of each of the two types, resulting a single main chain with multiple side chains.

Other schemes can also be carried out. For example, in accordance with the third strategy above, a first chain having reactive side groups can be reacted with a monomer, thus polymerizing the side chains in situ. As a specific example, poly(methylphenylsilane)-graft-poly(styrene) has reportedly been synthesized via ATRP, where bromomethylated poly(methylphenylsilane) is utilized as a macromolecular initiator in an ATRP of styrene. See S. J. Holder et al., "A convenient route to poly(methylphenylsilane)-graft-polystyrene copolymers," *Macromol. Chem. Phys.*, 1997, vol. 198, p. 3571.

As another example, and in accordance with the first strategy above, a first chain having a terminal reactive group is reacted with a second chain having a number of reactive side groups. As a specific example, hydrosylation chemistry can be used to construct a graft copolymer having a polysiloxane main chain and polystyrene side chains as follows (only a single polystyrene side chain is illustrated in this scheme):

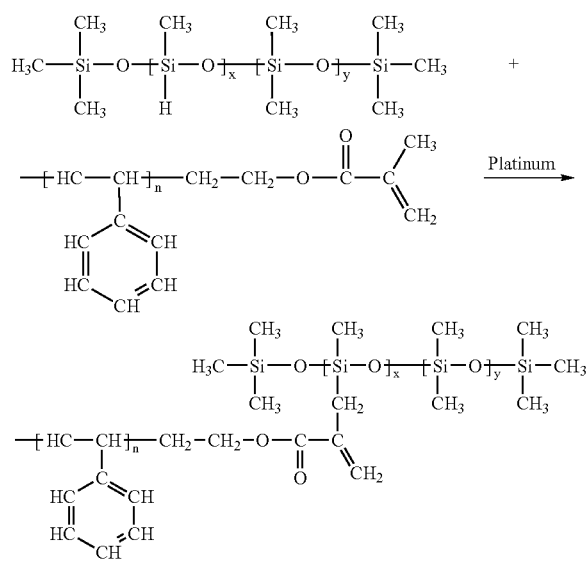

Implantable or insertable medical devices are typically sterilized by exposure to ethylene oxide or to radiation such as gamma or electron beam radiation. Certain therapeutic agents, however, are unstable under ethylene oxide sterilization conditions. On the other hand, radiation sterilization can lead to chain scission and/or crosslinking of polymers within the medical device, resulting in changes in the chemical, physical, and drug-eluting properties of the polymers. For example, the polyisobutylene center block of the SIBS copolymer can undergo significant changes in its chemical and physical properties upon exposure to radiation, especially at the levels used for sterilization of medical devices, which is on the order of 2.5 Mrad, due, for instance, to chain scission and/or crosslinking reactions. These reactions can alter the drug eluting properties of the SIBS copolymer and can lead to an unacceptable increase in the surface tack of the same, which can in turn lead to defects in the polymer upon expansion (for example, when the SIBS copolymer is in the form of a coating on the surface of an expandable stent or balloon). The present invention, on the other hand, allows soft blocks to be used that are more radiation resistant than polyisobutylene. Examples include polysiloxane and poly(acrylate-co-methacrylate) blocks. In some embodiments, for example, where chain scission and/or crosslinking of the main and/or side chains of the graft copolymers are not overly severe, any attendant changes in the chemical and physical properties of the polymer can be simply be anticipated and taken into account.

Once a desired graft copolymer is obtained, numerous techniques are available for forming the polymeric release regions of the present invention. For example, where the selected graft copolymer has thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the polymer prior to thermoplastic processing, producing a therapeutic-agent containing carrier region. If not, then a carrier region can nonetheless be formed by subsequent introduction of therapeutic agent as discussed below.

Polymeric release regions can also be formed using solvent-based techniques in which polymer is first dissolved in a solvent and the resulting mixture is subsequently used to form the polymeric release region.

Where solvent-based techniques are used, the solvent system that is selected will contain one or more solvent species. The solvent system preferably is a good solvent for the copolymer and, where included, for the therapeutic agent as well (although the therapeutic agent will merely be dispersed in the solvent in some embodiments). The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

Typically, a mixture containing solvent and copolymer is applied to a substrate to form a release region. For example, the substrate can be all or a portion of an implantable or insertable medical device to which the release layer is applied.

On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the copolymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are formed over a therapeutic-agent-containing region. In some embodiments, the therapeutic-agent-containing region will comprise one or more polymers, which can be selected, for example, from the polymers listed herein. As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

The polymeric release regions of the present invention can include one or more supplementary polymers, as desired, in addition to the graft copolymer. The supplementary polymers can be added, for example, to influence the strength or diffusion properties of the release layer.

The supplementary polymers may be, for example, homopolymers or copolymers, crosslinked or uncrosslinked, linear or branched, natural or synthetic, thermoplastic or thermosetting. Supplementary polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

The release profile associated with the release region can be modified in a number of ways, including (a) varying the type and/or molecular weight of the side chains and/or the main chains within the graft copolymer and (b) varying the type and/or molecular weight of any supplemental polymer that is added.

For instance, the hydrophilic/hydrophobic balance of the release region (and hence the release profile) can be varied by changing the monomers that are used to form the graft copolymer. As a first example, a graft copolymer can be provided, in which the main chain is provided with relatively hydrophilic units, as desired. For instance, the main chain of a graft copolymer with poly(ethyl acrylate) main chain and poly(styrene) side chains can be rendered more hydrophilic by substituting 2-hydroxyethyl methacrylate monomers for at least some of the ethyl acrylate monomers that are present. As a second example, a graft copolymer can be provided, in which the side chain is provided with relatively hydrophilic groups (e.g. polyethylene oxide or polyvinylpyrrolidone), as desired.

The hydrophilic/hydrophobic balance of the release region (and hence the release profile) can also be varied by adding a hydrophilic or hydrophobic supplemental polymer to the release region. For example, a polystyrene-polyisobutylene-polystyrene triblock copolymer (SIBS) such as that described above can be added to a graft copolymer having a poly(ethyl acrylate) main chain and poly(styrene) side. As a result, the polystyrene side chains of the graft copolymer and the polystyrene blocks of the SIBS will migrate into the same phase, altering the release profile. While not wishing to be bound by theory, it is believed that the addition of the SIBS will increase the hydrophobicity of the release layer, among other effects.

Medical devices having a sustained release profile are preferred in many cases. By "sustained release profile" is meant a release profile in which less than 25% of the total release from the medical device that occurs over the course of implantation/insertion in the body occurs within the first 1, 2, 3 or even more days of administration. Conversely, this means that more than 75% of the total release from the medical device will occur in a controlled fashion after the device has been implanted/inserted for the same period.

The release characteristics that are ultimately of interest are of course the release characteristics within the subject, for example, within a mammalian subject. However, it is well known in the art to test the release characteristics within an experimental system that gives a good indication of the actual release characteristics within the subject. For example, aqueous buffer systems are commonly used for testing release of therapeutic agents from vascular devices.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including aspirin and thienopyridine (ticlopidine, clopidogrel) and GP Ib/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

The invention is further described with reference to the following non-limiting Examples.

EXAMPLE 1

Synthesis and Characterization of a Carrier Layer Containing Paclitaxel and poly(ethylacrylate-graft-polystyrene)copolymer or poly(butylacrylate-graft-polystyrene)copolymer A two neck round bottom flask is charged with a magnetic stir bar and methacrylate-terminated polystyrene (1 gram). The flask is also equipped with a stopcock, a thermometer and reflux condenser, and a nitrogen inlet adapter is attached to the top of the reflux condenser. Inhibitor is removed from ethyl acrylate or butyl acrylate monomer by passing the ethyl or butyl acrylate monomer through an inhibitor removal column (Aldrich—306312). The ethyl or butyl acrylate monomer is then collected in a tared vial (9 grams). 2,2'-azobisisobutyronitrile (AIBN) is weighed out into a separate vial. The AIBN (0.106 grams) is dissolved in 1 ml of toluene. The ethyl or butyl acrylate monomer and the AIBN stock solution are then pipetted into the round bottom flask, after which an additional 49 ml of toluene are added, bringing the solution concentration to 19% solution (wt/wt). An additional procedure is conducted to form a poly(butyl acrylate)-g-poly(styrene) having an increased number of poly(styrene) grafts. In this procedure, 1.0 grams of the methacrylate-terminated polystyrene and 4.5 grams (18 wt % polystyrene) are copolymerized using AIBN (0.05 g) in toluene (27 ml).

The mixture is stirred until the methacrylate-terminated polystyrene dissolves. The system is purged with nitrogen for five minutes, after which the solution is sparged with nitrogen for two additional minutes. The solution is then heated to 65° C. for six hours and allowed to cool to room temperature. The solution is subsequently precipitated into ethanol.

The resulting poly(ethylacrylate-graft-polystyrene)copolymer is produced at a yield of 41%, contains 22.4 mol % polystyrene (NMR), has a polydispersity of 1.59 and the following molecular weights: Mn=65,000; Mw=104,000.

Solutions are provided that contain 5 wt % tetrahydrofuran (THF), 94 wt % toluene, 0.25 wt % paclitaxel and 0.75 wt % polymer. All solutions are prepared by (1) mixing the polymer with the toluene and heating to 70° C. for about an hour, (2) adding the THF, (3) adding the paclitaxel, (4) thoroughly mixing (e.g., overnight), and (5) filtering. The following solutions are made: (1) a solution containing 0.75 wt % poly(ethylacrylate-graft-polystyrene)copolymer, (2) a solution containing 0.75 wt/o poly(butylacrylate-graft-polystyrene)copolymer (10 wt % initial polystyrene), (3) a solution containing 0.75 wt % poly(butylacrylate-graft-polystyrene)copolymer (18 wt % initial polystyrene), and (4) a solution containing 0.75 wt % polystyrene-polyisobutylene-polystyrene triblock copolymers (SIBS), as described in United States Patent Application 20020107330 entitled "Drug delivery compositions and medical devices containing block copolymer."

Solutions are also provided that contain 5 wt % tetrahydrofuran (THF), 94 wt % toluene, 0.10 wt % paclitaxel and 0.90 wt % polymer. All solutions are prepared by (1) mixing the polymer with the toluene and heating to 70° C. for about an hour, (2) adding the THF, (3) adding the paclitaxel, (4) thoroughly mixing (e.g., overnight), and (5) filtering. The following solutions are made: (1) a solution containing 0.90 wt % poly(ethylacrylate-graft-polystyrene)copolymer, (2) a solution containing 0.90 wt % poly(butylacrylate-graft-polystyrene)copolymer (10 wt % initial polystyrene), (3) a solution containing 0.90 wt/o poly(butylacrylate-graft-polystyrene)copolymer (18 wt % initial polystyrene) and (4) a solution containing 0.90 wt % SIBS.

Each solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. 8 stents are formed in this manner for each of the solutions.

Microscopic evaluation pre- and post-expansion indicated that coating quality is good in all cases.

EXAMPLE 2

Synthesis and Characterization of Polydimethylsiloxane-Graft-Polystyrene Copolymer Polydimethylsiloxane-co-polystyrene graft copolymer is a thermoplastic elastomer where the polydimethylsiloxane segments are elastomeric and the polystyrene chains form physical crosslinks. The synthesis of this copolymer involves two steps. The first step involves synthesizing a polydimethylsiloxane macroinitiator. The graft copolymer is synthesized from a macroinitiator made from vinyl benzyl chloride and a polydimethylsiloxane-co-polymethylhydrogen siloxane. The benzyl chloride groups are located along the polymer backbone. This polydimethylsiloxane macroinitiator can then be used to polymerize styrene monomer using atom transfer radical polymerization (ATRP). The polystyrene chains will grow from the benzyl chloride initiating groups located on the polymer chain. The molecular weight of the polystyrene chains can be controlled using ATRP.

Macroinitiator synthesis. Inhibitor is removed from vinyl benzylchloride (m,p mers) by passing the vinyl benzylchloride through an inhibitor removal column (Aldrich—306312). The vinyl benzylchloride is collected in a tared vial. A two neck round bottom flask is charged with polydimethylsiloxane-co-polymethylhydrogensiloxane (MW=1,600, 25-30 mol % methylhydrogen siloxane), vinyl benzylchloride, toluene, and platinum catalyst (i.e., platinum-divinyltetramethyldisiloxane complex). The round bottom flask is also equipped with a stopcock. The flask is fitted with a magnetic stir bar, thermometer and reflux condenser, and the reaction mixture is stirred until the polystyrene dissolves. The solution is heated to 50° C. for one hour. The reaction is conducted under air. The solution is allowed to cool to room temperature and is precipitated into ethanol. The extent of reaction is determined by the disappearance of the silicone-hydride bond at 2158 cm$^{-1}$ using FT-IR. Another benzyl chloride-grafted polydimethylsiloxane macroinitiator is synthesized by the same procedure except that polydimethylsiloxane-co-polymethylhydrogen siloxane (0.5-1.0 mol % polymethylhydrogen siloxane (MW=55,000)) is used.

Copolymer synthesis. Inhibitor is removed from styrene by passing the styrene through a column of neutral alumina (Aldrich—199974). The styrene is collected in a tared vial. A two neck round bottom flask is fitted with a magnetic stir bar, thermometer and reflux condenser. The flask is charged with macroinitiator (see above), styrene, copper (I) chloride, and 4,4'-dinonyl-2,2'-bipyridine. The round bottom flask is also equipped with a stopcock. The reaction mixture is stirred until it turns dark red in color, after which the solution is sparged with nitrogen for thirty minutes. The reaction solution is heated to 130° C., and the reaction is allowed to proceed for twenty hours. The solution is then allowed to cool below 80° C. before adding toluene to dilute the polymer. Upon exposure to air the reaction solution turns green in color. The polymer solution is cooled to room temperature and passed through a column of neutral alumina to remove the metal complex. The polymer solution is then precipitated into ethanol and the polymer precipitate is filtered.

Stent coatings. Solutions are provided that contain 5 wt % tetrahydrofuran (THF), 94 wt % toluene, 0.25 wt % paclitaxel and 0.75 wt % polymer. All solutions are prepared by mixing the polymer with the toluene and heating to 70° C. for about an hour, adding the THF, adding the paclitaxel, thoroughly mixing (e.g., overnight), and filtering. The following solutions are made: (1) a solution containing 0.75 wt % polydimethylsiloxane-graft-polystyrene copolymer, and (2) a solution containing 0.75 wt % polystyrene-polyisobutylene-polystyrene triblock copolymer (SIBS), as described in United States Patent Application 20020107330 entitled "Drug delivery compositions and medical devices containing block copolymer."

Solutions are also provided that contain 5 wt % tetrahydrofuran (THF), 94 wt % toluene, 0.10 wt % paclitaxel and 0.90 wt % polymer. All solutions are prepared by mixing the polymer with the toluene and heating to 70° C. for about an hour, adding the THF, adding the paclitaxel, thoroughly mixing (e.g., overnight), and filtering. The following solutions are made: (1) a solution containing 0.90 wt % polydimethylsiloxane-graft-polystyrene copolymer, and (2) a solution containing 0.90 wt % SIBS.

Each solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. 8 stents are formed in this manner for each of the solutions.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a therapeutic agent and (b) a polymeric release region that controls the release of said therapeutic agent upon administration to a patient, said polymeric release region comprising a graft copolymer, which comprises a main chain and a plurality of side chains, wherein said main chain corresponds to a rubbery phase within said release region at ambient temperatures and comprises poly(methyl acrylate), poly(ethyl acrylate) or poly(butyl acrylate) and wherein said side chain corresponds to a hard phase within said release region at ambient temperatures and comprises poly(styrene) or poly(methyl methacrylate).

2. The implantable or insertable medical device of claim 1, wherein said polymeric release region further comprises a supplementary polymer in addition to said graft copolymer.

3. The implantable or insertable medical device of claim 1, wherein said medical device is sterilized using a quantity of radiation effective to kill pathogens.

4. The implantable or insertable medical device of claim 1, wherein said polymeric release region is a carrier region that comprises said therapeutic agent.

5. The implantable or insertable medical device of claim 1, wherein said polymeric release region is a barrier region disposed over a therapeutic-agent-containing region that comprises said therapeutic agent.

6. The implantable or insertable medical device of claim 1, wherein said polymeric release region is in the form of a coating layer.

7. The implantable or insertable medical device of claim 1, wherein said implantable or insertable medical device is adapted for implantation or insertion into the coronary vasculature, peripheral vascular system, esophagus, trachea, colon, biliary tract, urinary tract, prostate or brain.

8. The implantable or insertable medical device of claim 1, wherein said therapeutic agent is selected from one or more of the group consisting of an anti-thrombotic agent; an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

9. The implantable or insertable medical device of claim 1, wherein said wherein said implantable or insertable medical device is adapted for implantation or insertion into the coronary vasculature or peripheral vascular system.

10. The implantable or insertable medical device of claim 9, wherein said wherein said implantable or insertable medical device is a stent.

11. An implantable or insertable medical device comprising (a) a therapeutic agent and (b) a polymeric release region that controls the release of said therapeutic agent upon administration to a patient, said polymeric release region comprising a graft copolymer, which comprises a main chain and a plurality of side chains, wherein one of said main chain and said side chains corresponds to a rubbery phase within said release region at ambient temperatures, wherein the other of said main chain and said side chains corresponds to a hard phase within said release region at ambient temperatures, and wherein said graft copolymer is selected from polyethylacrylate-graft-polystyrene copolymer, polybutylacrylate-graft-polystyrene copolymer, and polydimethylsiloxane-graft-polystyrene copolymer.

12. The implantable or insertable medical device of claim 1, wherein said medical device is selected from a guide wire, a catheter, a balloon, a vena cava filter, a stent, a stent graft, a Vascular graft, a cerebral aneurysm filler coil, a pacemaker lead, a myocardial plug, a heart valve, and a shunt.

13. The implantable or insertable medical device of claim 11, wherein said polymeric release region further comprises a supplementary polymer in addition to said graft copolyrner.

14. The implantable or insertable medical device of claim 11, wherein said polymeric release region is a carrier region that comprises said therapeutic agent.

15. The implantable or insertable medical device of claim 11, wherein said polymeric release region is a barrier region disposed over a therapeutic-agent-containing region that comprises said therapeutic agent.

16. The implantable or insertable medical device of claim 11, wherein said polymeric release region is in the form of a coating layer.

17. The implantable or insertable medical device of claim 11, wherein said implantable or insertable medical device is adapted for implantation or insertion into the coronary vasculature, peripheral vascular system, esophagus, trachea, colon, biliary tract, urinary tract, prostate or brain.

18. The implantable or insertable medical device of claim 11, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

19. The implantable or insertable medical device of claim 11, wherein said wherein said implantable or insertable medical device is adapted for implantation or insertion into the coronary vasculature or peripheral vascular system.

20. The implantable or insertable medical device of claim 19, wherein said wherein said implantable or insertable medical device is a stent.

21. The implantable or insertable medical device of claim 11, wherein said medical device is selected from a guide wire, a catheter, a balloon, a vena cava filter, a stent, a stent graft, a vascular grail, a cerebral aneurysm filler coil, a pacemaker lead, a myocardial plug, a heart valve, and a shunt.

* * * * *

UNITED STATES PATENT AND TRADEMARK OFFICE
CERTIFICATE OF CORRECTION

| | | |
|---|---|---|
| PATENT NO. | : 7,357,940 B2 | Page 1 of 6 |
| APPLICATION NO. | : 10/632413 | |
| DATED | : April 15, 2008 | |
| INVENTOR(S) | : Robert E. Richard et al. | |

It is certified that error appears in the above-identified patent and that said Letters Patent is hereby corrected as shown below:

Col. 1, line 56, after "lower", change "that" to --than--.

Col. 2, line 50, after "chain", change "in situ" to --*in situ*--.

Col. 2, line 50, after "chain", change "in situ" to --*in situ*--.

Col. 3, line 51, after first word "or", add --more--.

Col. 4, line 43, after "elimination", add --of--.

Col. 5, line 6, after "and/or", change "vice versa" to --*vice versa*--.

Col. 6, lines 6/7, change last/first word "3-methylsytrene" to --3-methylstyrene-- and after "($T_g$ 97° C.)", first occurrence, change "4-methylsytrene" to --4-methylstyrene--.

Col. 6, lines 7/8, change last/first word "2,4-dimethylsytrene" to --2,4-dimethylstyrene-- and after "($T_g$ 112° C.)", change "2,5-dimethylsytrene" to --2,5-dimethylstyrene--.

Col. 6, line 9, after first word "C.),", change "3,5-dimethylsytrene" to --3,5-dimethylstyrene--.

Col. 6, lines 9/10, change last/first word "2,4,6-trimethylsytrene" to --2,4,6-trimethylstyrene--.

Col. 6, lines 11/12, change last/first word "4-methoxysytrene" to --4-methoxystyrene-- and after "($T_g$ 113° C.) and", change "4-ethoxysytrene" to --4-ethoxystyrene--.

UNITED STATES PATENT AND TRADEMARK OFFICE
CERTIFICATE OF CORRECTION

PATENT NO. : 7,357,940 B2
APPLICATION NO. : 10/632413
DATED : April 15, 2008
INVENTOR(S) : Robert E. Richard et al.

It is certified that error appears in the above-identified patent and that said Letters Patent is hereby corrected as shown below:

Col. 6, line 13, change last word "2-chlorosytrene" to --2-chlorostyrene--.

Col. 6, line 14, change last word "4-chlorosytrene" to --4-chlorostyrene--.

Col. 6, line 15, change "($T_g$ 100° C.), 2,6-dichlorosytrene" to --($T_g$ 110° C.), 2,6-dichlorostyrene--.

Col. 6, line 22, change last words "vinyl private ($T_g$" to --vinyl pivalate ($T_g$--.

Col. 6, line 29, after "ether", change "($T_g$ -3°° C.)" to --($T_g$ -31° C.)--.

Col. 7, line 13, after "acrylate", first occurrence, change "($T_g$ 110° C.)" to --($T_g$ 10° C.)--, Col. 8, line 25, after "chain", change "in situ" to --*in situ*--.

Col. 8, lines 29/30, change last/first words "in situ" to --*in situ*--.

Col. 8, line 42, after "chain", change "monomer" to --monomers--.

Col. 9, lines 1-33, change "

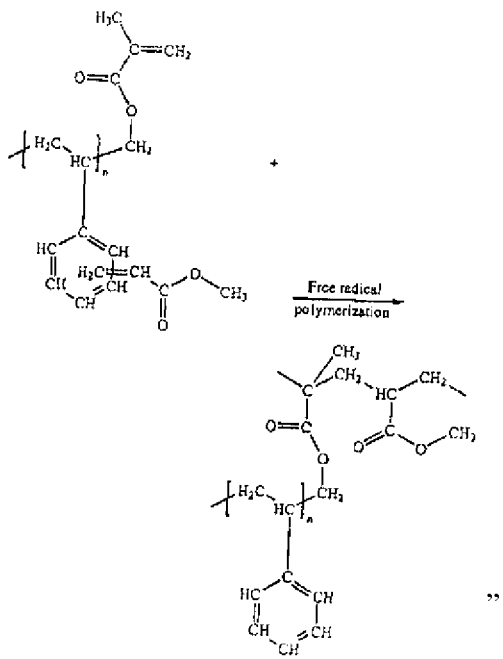

"

UNITED STATES PATENT AND TRADEMARK OFFICE
CERTIFICATE OF CORRECTION

PATENT NO. : 7,357,940 B2
APPLICATION NO. : 10/632413
DATED : April 15, 2008
INVENTOR(S) : Robert E. Richard et al.

It is certified that error appears in the above-identified patent and that said Letters Patent is hereby corrected as shown below:

to --
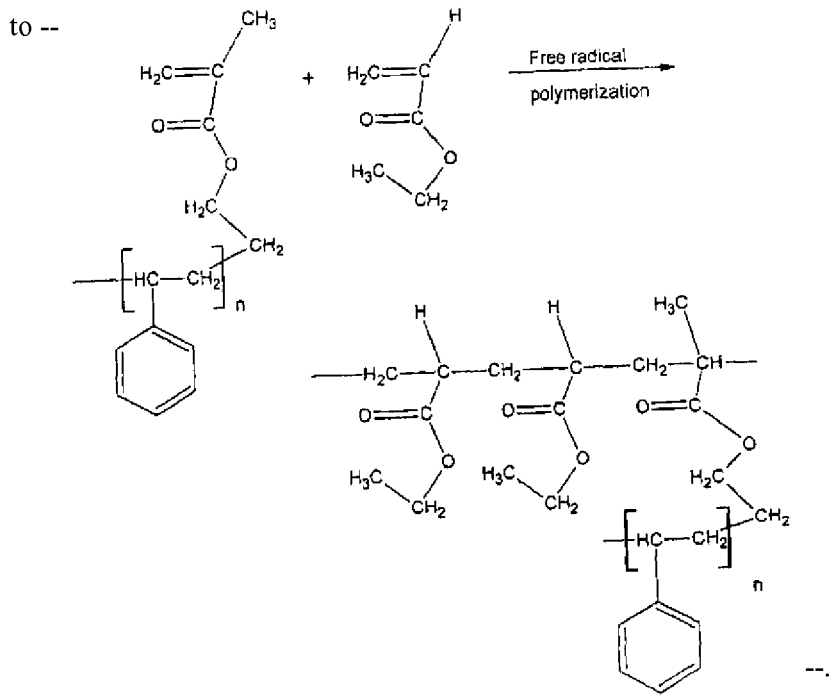
--.

Col. 10, line 26, after "resulting", add --in--.

Col. 11, line 3, after "resulting", add --in--.

Col. 11, line 8, after "chains", change "in situ" to --*in situ*--.

UNITED STATES PATENT AND TRADEMARK OFFICE
CERTIFICATE OF CORRECTION

PATENT NO. : 7,357,940 B2
APPLICATION NO. : 10/632413
DATED : April 15, 2008
INVENTOR(S) : Robert E. Richard et al.

It is certified that error appears in the above-identified patent and that said Letters Patent is hereby corrected as shown below:

Col. 11, lines 25-48, change

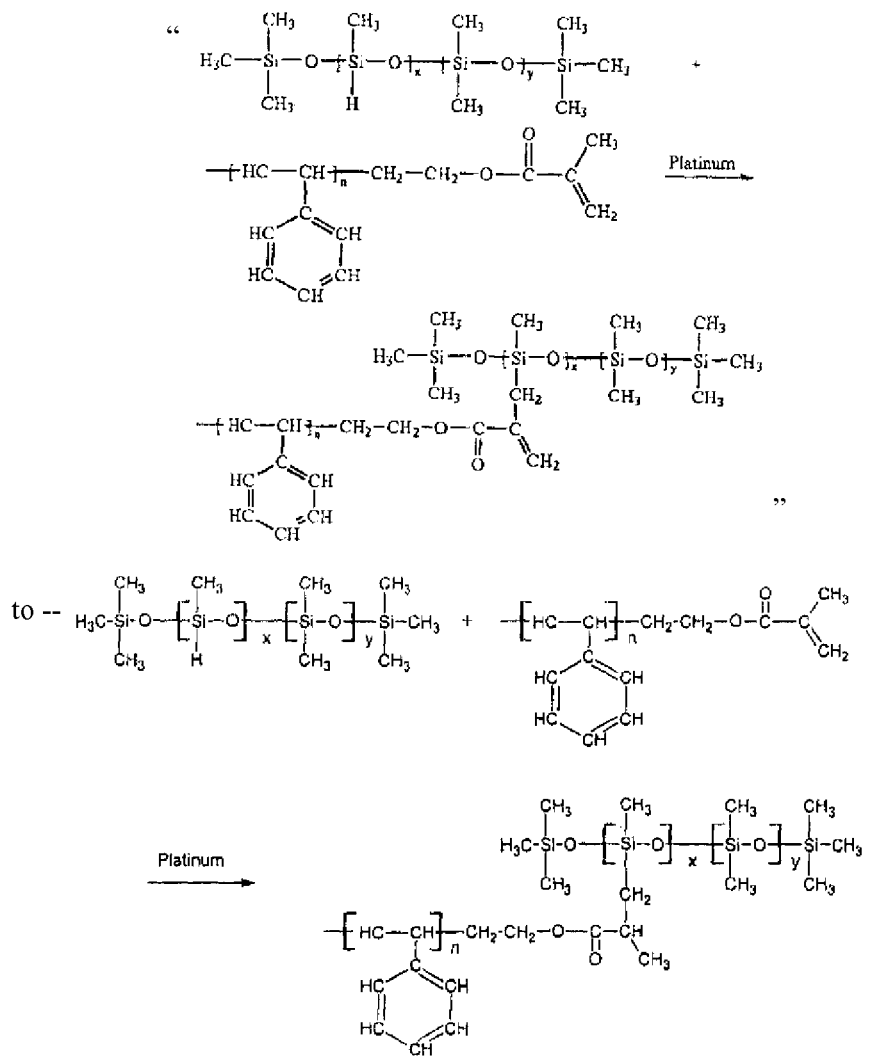

UNITED STATES PATENT AND TRADEMARK OFFICE
CERTIFICATE OF CORRECTION

| | | |
|---|---|---|
| PATENT NO. | : 7,357,940 B2 | |
| APPLICATION NO. | : 10/632413 | |
| DATED | : April 15, 2008 | |
| INVENTOR(S) | : Robert E. Richard et al. | |

It is certified that error appears in the above-identified patent and that said Letters Patent is hereby corrected as shown below:

Col. 11, line 63, after "the", first occurrence, change "drug eluting" to --drug-eluting--.

Col. 12, line 8, after "can", delete "be".

Col. 13, line 54, after "and", change "hydoxyalkyl" to --hydroxyalkyl--.

Col. 18, lines 47/48, after "resulting", change last/first words "poly(ethylacrylate-graft-polystyrene)copolymer" to -- poly(ethylacrylate-graft-polystyrene) copolymer--.

Col. 18, line 58, after "wt %", change "poly(ethylacrylate-graft-polystyrene)copolymer" to --poly(ethylacrylate-graft-polystyrene) copolymer--.

Col. 18, lines 59/60, after "0.75", change "wt/o poly(butylacrylate-graft-polystyrene)copolymer" to --wt % poly(butylacrylate-graft-polystyrene) copolymer--.

Col. 18, lines 61/62, after "0.75 wt %", change "poly(butylacrylate-graft-polystyrene)copolymer" to --poly(butylacrylate-graft-polystyrene) copolymer--.

Col. 19, lines 9/10, after "0.90 wt %", change "poly(butylacrylate-graft-polystyrene)copolymer" to --poly(butylacrylate-graft-polystyrene) copolymer--.

UNITED STATES PATENT AND TRADEMARK OFFICE
CERTIFICATE OF CORRECTION

PATENT NO. : 7,357,940 B2
APPLICATION NO. : 10/632413
DATED : April 15, 2008
INVENTOR(S) : Robert E. Richard et al.

It is certified that error appears in the above-identified patent and that said Letters Patent is hereby corrected as shown below:

Col. 19, lines 11/12, after "0.90", change "wt/o" to --wt %--.

Col. 19, line 49, after first word "benzylchloride", change "(m,p mers)" to --(*m, p* isomers)--.

Claim 9, Col. 21, line 41, after first word "1,", delete "wherein said", first occurrence.

Claim 10, Col. 21, line 45, after first word "9,", delete "wherein said", first occurrence.

Claim 12, Col. 22, line 9, after first word "a", change "Vascular" to --vascular--.

Claim 19, Col. 22, line 42, after first word "11,", delete "wherein said", first occurrence.

Claim 20, Col. 22, line 46, after first word "19,", delete "wherein said", first occurrence.

Claim 21, Col. 22, line 51, after "vascular", change "grail" to --graft--.

Signed and Sealed this

Twenty-eighth Day of July, 2009

JOHN DOLL
*Acting Director of the United States Patent and Trademark Office*